(12) United States Patent
Spector et al.

(10) Patent No.: US 12,218,537 B2
(45) Date of Patent: Feb. 4, 2025

(54) WEARABLE ELECTRONIC DEVICE CHARGING UNIT

(71) Applicant: RESO-SENSE LTD, Kfar Hess (IL)

(72) Inventors: Yuval Spector, Bahan (IL); Asaf Bar-David, Kfar Hess (IL)

(73) Assignee: RESO-SENSE LTD, Kfar Hess (IL)

( * ) Notice: Subject to any disclaimer, the term of this patent is extended or adjusted under 35 U.S.C. 154(b) by 0 days.

(21) Appl. No.: 18/574,770

(22) PCT Filed: Jun. 30, 2022

(86) PCT No.: PCT/IL2022/050702
§ 371 (c)(1),
(2) Date: Dec. 28, 2023

(87) PCT Pub. No.: WO2023/275874
PCT Pub. Date: Jan. 5, 2023

(65) Prior Publication Data
US 2024/0275186 A1    Aug. 15, 2024

Related U.S. Application Data

(60) Provisional application No. 63/273,953, filed on Oct. 31, 2021, provisional application No. 63/228,624, (Continued)

(51) Int. Cl.
*H02J 7/00* (2006.01)
*H01M 50/247* (2021.01)
(Continued)

(52) U.S. Cl.
CPC ......... *H02J 7/0042* (2013.01); *H01M 50/247* (2021.01); *H01M 50/262* (2021.01);
(Continued)

(58) Field of Classification Search
None
See application file for complete search history.

(56) References Cited

U.S. PATENT DOCUMENTS 10,032,557 B1 *  7/2018  Bossetti .............. H02J 50/12
10,849,392 B1 * 12/2020  Wittenberg ......... H01M 50/503
(Continued)

FOREIGN PATENT DOCUMENTS

WO      2016179030 A1    11/2016

*Primary Examiner* — Arun C Williams
(74) *Attorney, Agent, or Firm* — S. J. INTELLECTUAL PROPERTY; Avi Jencmen

(57) ABSTRACT

The presently disclosed subject matter aims to provide a wearable electronic device charging unit configured to be fastened onto a wearable electronic device strap attached to a wearable electronic device case, the wearable electronic device charging unit comprising: a power source; and, at least one attaching element coupled to the power source configured to attach the power source onto the wearable electronic device strap; wherein the power source is configured to be in an electrical communication with a rechargeable battery located within the wearable electronic device case so as to recharge the rechargeable battery without interfering with the operation of one or more power-consuming components located on the wearable electronic device case.

20 Claims, 6 Drawing Sheets

Related U.S. Application Data filed on Aug. 3, 2021, provisional application No. 63/217,303, filed on Jul. 1, 2021.

(51) Int. Cl.
  *H01M 50/262*  (2021.01)
  *H02J 50/10*  (2016.01)
  *G06F 1/16*  (2006.01)

(52) U.S. Cl.
  CPC ............ *H02J 7/0048* (2020.01); *H02J 50/10* (2016.02); *G06F 1/163* (2013.01)

(56) References Cited

U.S. PATENT DOCUMENTS

| | | |
|---|---|---|
| 11,394,215 B1* | 7/2022 | Bhagwan .............. H02J 7/0063 |
| 2015/0349457 A1 | 12/2015 | Shariff et al. |
| 2016/0091922 A1 | 3/2016 | Nazzaro et al. |
| 2016/0291550 A1 | 10/2016 | Chen et al. |
| 2017/0033567 A1 | 2/2017 | Adamisin |
| 2019/0137948 A1* | 5/2019 | Yaghmour ............ G06F 1/1632 |
| 2019/0140479 A1 | 5/2019 | Henry et al. |
| 2020/0073337 A1 | 3/2020 | Wang |
| 2020/0343745 A1 | 10/2020 | Choi |

\* cited by examiner

WEARABLE ELECTRONIC DEVICE CHARGING UNIT

TECHNICAL FIELD

The present invention relates to the field of systems and methods for charging wearable electronic devices.

BACKGROUND

Wearable electronic devices are smart electronic devices (electronic devices with micro-controllers) worn on the skin's surface, where they detect, analyze, and transmit information concerning, e.g., body signals such as vital signs, and/or ambient data, which allow immediate biofeedback to the wearer.

With the advancement of wearable electronic devices, many functionally oriented devices, such as smartwatches or smart wristbands having functions such as GPS (Global Positioning System), heartbeat sensing, pace counting, and the like, have become more and more popular among consumers. However, these devices tend to consume a substantial amount of power.

Due to the limited size of wearable electronic devices, the capacities of batteries installed therein cannot be large, forcing the users to charge their electronic devices more frequently.

There is thus a need in the art for a new wearable electronic device charging unit.

GENERAL DESCRIPTION

In accordance with a first aspect of the presently disclosed subject matter, there is provided a wearable electronic device charging unit configured to be fastened onto a wearable electronic device strap, attached to a wearable electronic device case, the wearable electronic device charging unit comprising: a power source; and, at least one securing element coupled to said power source configured to attach said power source onto said wearable electronic device strap; wherein said power source is configured to be in an electrical communication with a rechargeable battery located within said wearable electronic device case so as to recharge said rechargeable battery without interfering with the operation of one or more power-consuming components located on said wearable electronic device case.

In some cases, the one or more power-consuming components are sensors.

In some cases, the electrical communication is achieved through an electrical wire being in communication with said power source configured to connect said power source to the rechargeable battery.

In some cases, the connection of said power source to said rechargeable battery is formed at the bottom or side surfaces of said wearable electronic device case.

In some cases, the wearable electronic device case includes at least one electrical connector at its bottom or side surfaces configured to enable said electrical wire to interact with said rechargeable battery located within said wearable electronic device case.

In some cases, the electrical wire includes a designated plug at its distal end configured to interact with said at least one electrical connector.

In some cases, the electrical wire extends between the wearable electronic device charging unit and the rechargeable battery of the wearable electronic device case along the bottom surface of the wearable electronic device strap, without being visible.

In some cases, the wearable electronic device is one of: a smartwatch, a pulse watch, a fitness tracker, or a watch phone.

In some cases, the electrical wire is coated with an isolated material.

In some cases, the electrical wire is made of a flexible material.

In some cases, the securing element is made of a flexible material.

In some cases, the flexible material is stretchable.

In some cases, the securing element is a loop keeper configured to allow said wearable electronic device strap to pass therethrough it.

In some cases, the power source is situated within a designated housing.

In some cases, the housing is made of a rigid material.

In some cases, the housing is made of a semi-rigid material.

In some cases, the power source further includes an indicator indicative of the state of said rechargeable battery.

In some cases, the indicator is configured to indicate the remaining power of said power source.

In some cases, the indicator includes at least one light source configured to provide a visual display of said remaining power of said power source.

In some cases, the least one light source is a light emitting diode (LED).

In some cases, the charge involves wireless charging.

In some cases, the wireless charging is achieved using a wireless charger adapter containing an inductive coil directed to form an electrical induction through which the power source charges the rechargeable battery within the wearable electronic device case.

In some cases, the wireless charger adapter includes one or more apertures positioned correspondingly to the location of said one or more power-consuming components.

In some cases, the wireless charger adapter includes a transparent region positioned correspondingly to the location of said one or more power-consuming components.

In some cases, the wireless charger adapter is fitted on the bottom surface of said wearable electronic device case.

In some cases, the wireless charger adapter is fitted on the bottom surface of said wearable electronic device case using fitting means.

In some cases, the inductive coil is attached to the bottom surface of the wearable electronic device case using a fastening element.

In some cases, the fastening element is a magnet.

In some cases, the inductive coil is attached to the bottom surface of the wearable electronic device case element using a designated mechanical fitting which wraps the bottom surface of the wearable electronic device case, holding the inductive coil therebetween the surface of wearable electronic device case and the designated mechanical fitting.

In some cases, the wireless charger adapter includes a thermocouple placed in close proximity to the inductive coil so as to provide real-time temperature measurements of the wireless charger adapter's surface.

In accordance with a second aspect of the presently disclosed subject matter, there is provided a wearable electronic device charging unit configured to be fastened onto a wearable electronic device strap attached to a wearable electronic device case, the wearable electronic device charging unit comprising: a power source configured to be in an electrical communication with a rechargeable battery located within said wearable electronic device case so as to recharge said rechargeable battery without interfering with the operation of one or more sensors located on said wearable electronic device case; at least one securing element coupled to said power source configured to attach said power source onto said wearable electronic device strap; and, a processing circuitry configured to: obtain information from said rechargeable battery located within said wearable electronic device case regarding its power level; compare said information to a threshold; and, based on the result of the comparison, initiate an electrical current transferring from said wearable electronic device charging unit to said rechargeable battery.

In some cases, the electrical communication is achieved through an electrical wire being in communication with said power source configured to connect said power source to the rechargeable battery.

In some cases, the connection of said power source to said rechargeable battery is formed at the bottom or side surfaces of said wearable electronic device case.

In some cases, the wearable electronic device case includes at least one electrical connector at its bottom or side surfaces configured to enable said electrical wire to interact with said rechargeable battery located within said wearable electronic device case.

In some cases, the electrical wire includes a designated plug at its distal end configured to interact with said at least one electrical connector.

In some cases, the electrical wire extends between the wearable electronic device charging unit and the rechargeable battery of the wearable electronic device case along the bottom surface of the wearable electronic device strap, without being visible.

In some cases, the wearable electronic device is one of: a smartwatch, a pulse watch, a fitness tracker, or a watch phone.

In some cases, the electrical wire is coated with an isolated material.

In some cases, the electrical wire is made of a flexible material.

In some cases, the securing element is made of a flexible material.

In some cases, the flexible material is stretchable.

In some cases, the securing element is a loop keeper configured to allow said wearable electronic device strap to pass therethrough it.

In some cases, the power source is situated within a designated housing.

In some cases, the housing is made of a rigid material.

In some cases, the housing is made of a semi-rigid material.

In some cases, the power source further includes an indicator indicative of the state of said rechargeable battery.

In some cases, the indicator is configured to indicate the remaining power of said power source.

In some cases, the indicator includes at least one light source configured to provide a visual display of said remaining power of said power source.

In some cases, the least one light source is a light emitting diode (LED).

In some cases, the charge involves wireless charging.

In some cases, the wireless charging is achieved using a wireless charger adapter containing an inductive coil directed to form an electrical induction through which the power source charges the rechargeable battery within the wearable electronic device case.

In some cases, the inductive coil is attached to the bottom surface of the wearable electronic device case using a fastening element.

In some cases, the fastening element is a magnet.

In some cases, the inductive coil is attached to the bottom surface of the wearable electronic device case element using a designated mechanical fitting which wraps the bottom surface of the wearable electronic device case, holding the inductive coil therebetween the surface of wearable electronic device case and the designated mechanical fitting.

In some cases, the wireless charger adapter includes one or more apertures positioned correspondingly to the location of said one or more power-consuming components.

In some cases, the wireless charger adapter includes a transparent region positioned correspondingly to the location of said one or more power-consuming components.

In some cases, the wireless charger adapter is fitted on the bottom surface of said wearable electronic device case.

In some cases, the wireless charger adapter is fitted on the bottom surface of said wearable electronic device case using fitting means.

In some cases, the wireless charger adapter includes a thermocouple placed in close proximity to the inductive coil so as to provide real-time temperature measurements of the wireless charger adapter's surface.

BRIEF DESCRIPTION OF THE DRAWINGS

In order to understand the presently disclosed subject matter and to see how it may be carried out in practice, the subject matter will now be described, by way of non-limiting examples only, with reference to the accompanying drawings, in which.

DETAILED DESCRIPTION

Figure 1:
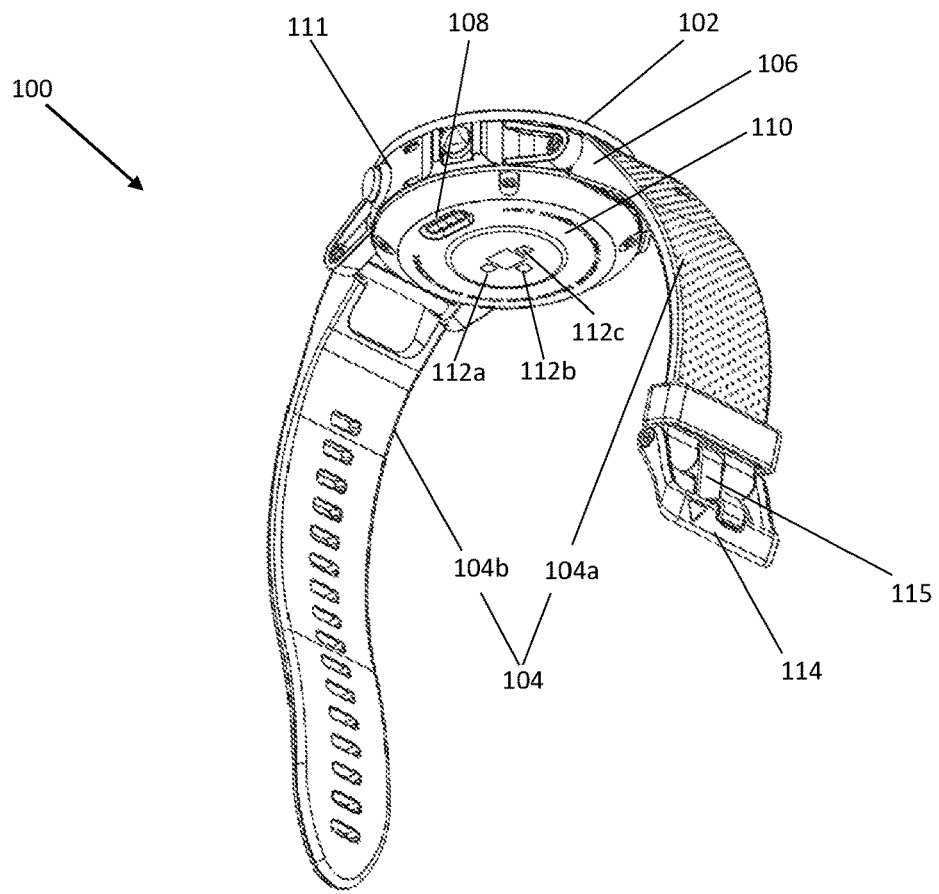
FIG. 1 is a schematic illustration of a wearable electronic device, in accordance with the presently disclosed subject matter.

In the following detailed description, numerous specific details are set forth in order to provide a thorough understanding of the presently disclosed subject matter. However, it will be understood by those skilled in the art that the presently disclosed subject matter may be practiced without these specific details. In other instances, well-known methods, procedures, and components have not been described in detail so as not to obscure the presently disclosed subject matter.

In the drawings and descriptions set forth, identical reference numerals indicate those components that are common to different embodiments or configurations.

Unless specifically stated otherwise, as apparent from the following discussions, it is appreciated that throughout the specification discussions utilizing terms such as "obtaining", "comparing", "initiating", or the like, include action and/or processes of a computer that manipulate and/or transform data into other data, said data represented as physical quantities, e.g., such as electronic quantities, and/or said data representing the physical objects. The terms "computer", "processor", "processing resource", "processing circuitry", and "controller" should be expansively construed to cover any kind of electronic device with data processing capabilities, including, by way of non-limiting example, a personal desktop/laptop computer, a server, a computing system, a communication device, a smartphone, a tablet computer, a smart television, a processor (e.g. digital signal processor (DSP), a microcontroller, a field programmable gate array (FPGA), an application specific integrated circuit (ASIC), etc.), a group of multiple physical machines sharing performance of various tasks, virtual servers co-residing on a single physical machine, any other electronic computing device, and/or any combination thereof.

The operations in accordance with the teachings herein may be performed by a computer specially constructed for the desired purposes or by a general-purpose computer specially configured for the desired purpose by a computer program stored in a non-transitory computer readable storage medium. The term "non-transitory" is used herein to exclude transitory, propagating signals, but to otherwise include any volatile or non-volatile computer memory technology suitable to the application.

As used herein, the phrase "for example," "such as", "for instance" and variants thereof describe non-limiting embodiments of the presently disclosed subject matter. Reference in the specification to "one case", "some cases", "other cases" or variants thereof means that a particular feature, structure or characteristic described in connection with the embodiment(s) is included in at least one embodiment of the presently disclosed subject matter. Thus, the appearance of the phrase "one case", "some cases", "other cases" or variants thereof does not necessarily refer to the same embodiment(s).

It is appreciated that, unless specifically stated otherwise, certain features of the presently disclosed subject matter, which are, for clarity, described in the context of separate embodiments, may also be provided in combination in a single embodiment. Conversely, various features of the presently disclosed subject matter, which are, for brevity, described in the context of a single embodiment, may also be provided separately or in any suitable sub-combination.

Figure 6:
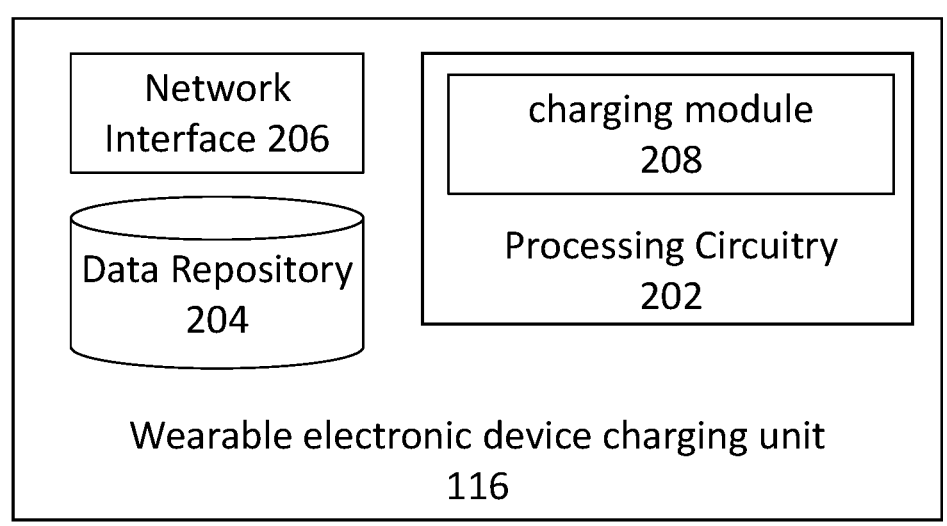
FIG. 6 is a block diagram schematically illustrating one example of a wearable electronic device charging unit, in accordance with the presently disclosed subject matter; and, FIG. 7 is a flowchart illustrating one example of a sequence of operations carried out by a wearable electronic device charging unit, in accordance with the presently disclosed subject matter.
Figure 7:
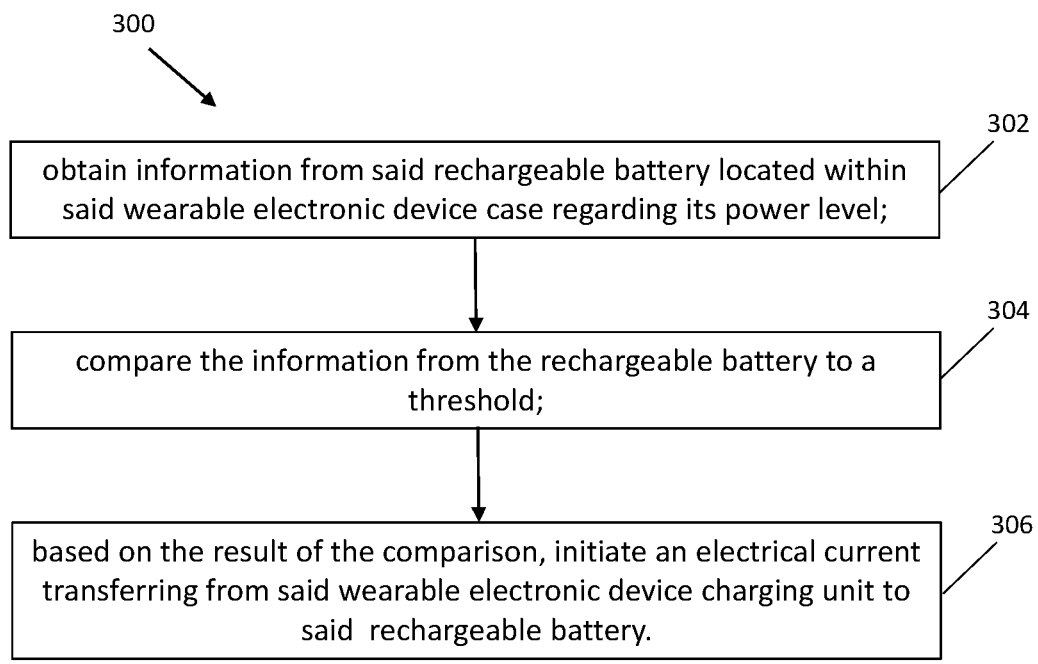

In embodiments of the presently disclosed subject matter, fewer, more and/or different stages than those shown in FIG. 7 may be executed. In embodiments of the presently disclosed subject matter one or more stages illustrated in FIG. 7 may be executed in a different order and/or one or more groups of stages may be executed simultaneously. FIGS. 1, 2A-2D, 3-4 and 5A-5B illustrate a general schematic of the system architecture in accordance with an embodiment of the presently disclosed subject matter. Each module in FIG. 6 can be made up of any combination of software, hardware and/or firmware that performs the functions as defined and explained herein. The modules in FIG. 6 may be centralized in one location or dispersed over more than one location. In other embodiments of the presently disclosed subject matter, the system may comprise fewer, more, and/or different modules than those shown in FIG. 6.

Any reference in the specification to a method should be applied mutatis mutandis to a system capable of executing the method and should be applied mutatis mutandis to a non-transitory computer readable medium that stores instructions that once executed by a computer result in the execution of the method.

Any reference in the specification to a system should be applied mutatis mutandis to a method that may be executed by the system and should be applied mutatis mutandis to a non-transitory computer readable medium that stores instructions that may be executed by the system.

Any reference in the specification to a non-transitory computer readable medium should be applied mutatis mutandis to a system capable of executing the instructions stored in the non-transitory computer readable medium and should be applied mutatis mutandis to method that may be executed by a computer that reads the instructions stored in the non-transitory computer readable medium.

By way of introduction, as shown in the schematic illustration of FIG. 1, a wearable electronic device, for example, wearable electronic device 100 (e.g., a smartwatch, a pulse watch, a fitness tracker, a watch phone, and the like) may be composed of a wearable electronic device case 102 and a wearable electronic device strap 104.

The wearable electronic device case 102 may include: (i) a cavity 106 housing a battery, for example, a rechargeable battery (not shown), (ii) at least one electrical connector or wireless charging feature, for example, electrical connector 108, positioned on one of the wearable electronic device case's surfaces (e.g., bottom surface 110, side surface 111, etc.), and (iii) at least one power-consuming component, for example, sensors 112a-112c, situated on one or more of the wearable electronic device case's surfaces (e.g., bottom surface 110). The electrical connector 108 may enable the formation of electrical interaction with the rechargeable battery housed within cavity 106, while sensors 112a-112c (which can be any one of an accelerometer, an ambient temperature sensor, a gyroscope, and the like) may provide wearable electronic device case 102 with information regarding measurable characteristics associated with a user of the wearable electronic device 100 (e.g., pulse rate, body temperature, blood pressure, and the like).

The wearable electronic device strap 104 may consist of one or more strap portions, for example, strap portions 104a-104b, attached to wearable electronic device case 102 from opposite directions, through at least one of their ends. The strap portions 104a-104b, which can be made of various material types, e.g., leather, plastic, rubber, cloth, and the like, may be fastened together and secured around a user's designated body part, for example, around the user's wrist, using any fastening means known in the art (e.g., hook and loop fasteners, snap fasteners, buckles, and the like).

By way of example, wearable electronic device 100 is a smartwatch having a round-shaped case 102 connected on its one end to a first leather-made strap portion 104a and on its other end to a second leather-made strap portion 104b. The first leather-made strap portion 104a includes a buckle 114 having a prong 115, whereas the second leather-made strap portion 104b includes a plurality of holes, equally spaced apart from one another, directed to receive prong 115.

To fasten the wearable electronic device 100 around a user's wrist, the wearable electronic device case 102 is placed on the upper end of the user's wrist, such that its bottom surface 110 is touching the user's wrist, while a portion of the second leather-made strap portion 104b including several holes out of the plurality of holes is passed therethrough buckle 114. This action is followed by the insertion of prong 115 therethrough a hole of the number of holes, such that both strap portions 104a-104b are now fastened together, wrapping the user's wrist.

Bearing this in mind, attention is drawn to FIGS. 2A-2D, showing schematic illustrations of a wearable electronic device charging unit and its operation as it is fastened onto a wearable electronic device strap 104, in accordance with the presently disclosed subject matter.

Figure 2A:
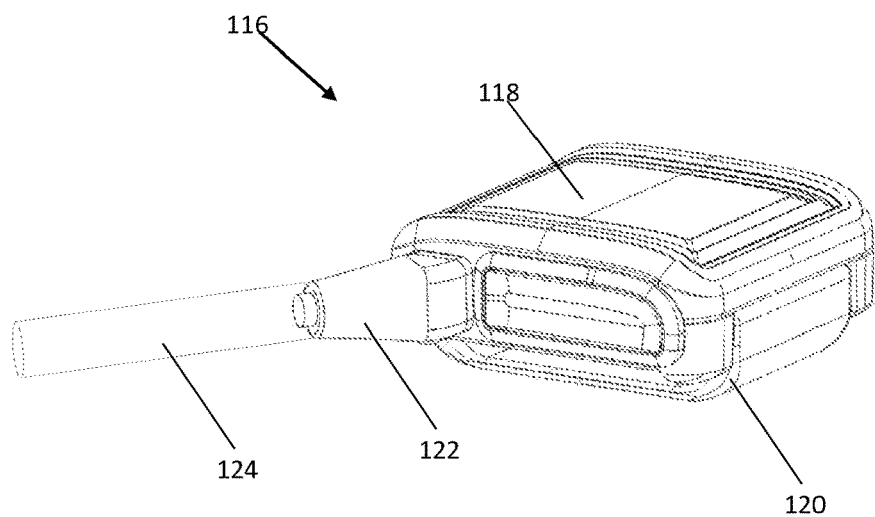
FIGS. 2A-2D and 4 are schematic illustrations of a wearable electronic device charging unit and its operation as it is fastened onto a wearable electronic device strap, in accordance with the presently disclosed subject matter.

As shown in the schematic illustration of FIG. 2A, wearable electronic device charging unit 116 includes (i) a power source, for example, power source 118, and (ii) at least one securing element, for example, securing element 120, coupled to power source 118.

Figure 2B:
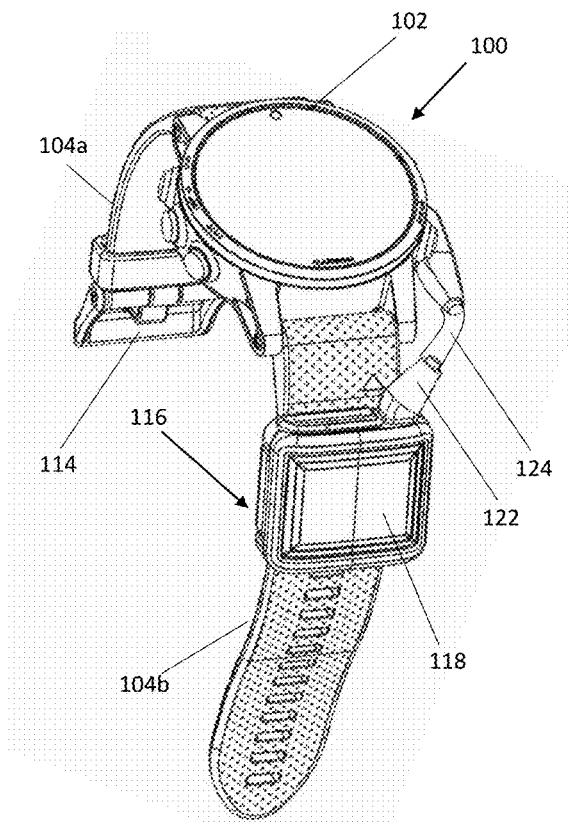
Figure 2C:
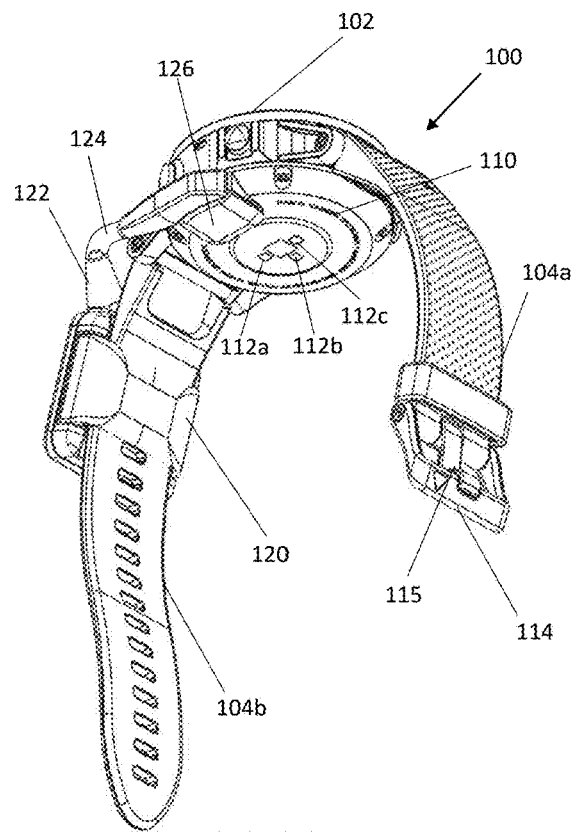
Figure 2D:
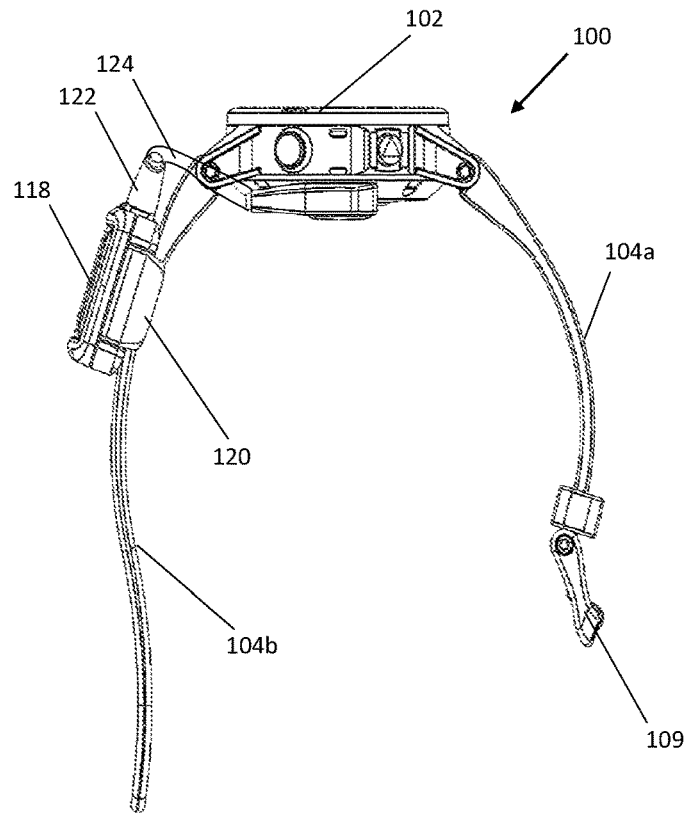
Figure 3:
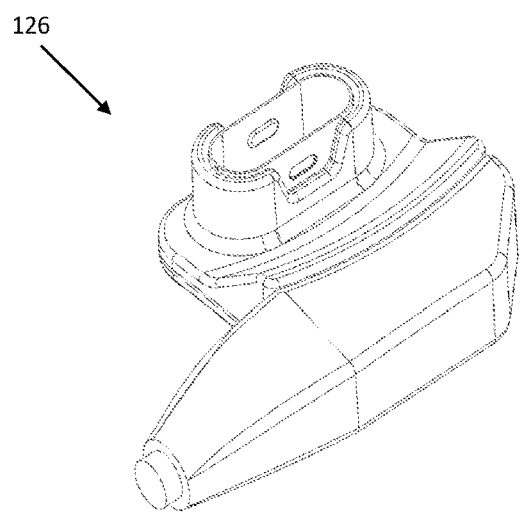
FIG. 3 is a schematic illustration of a designated plug positioned on the distal end of an electrical wire, in accordance with the presently disclosed subject matter.

Securing element 120, which may involve any securing means known in the art (e.g., hook-and-loop fasteners, buckle fasteners, keeper loops, and the like) and be made of different materials (such as a flexible material, a semi-flexible material, a stretchable material, and the like) and different dimensions and shapes (e.g., a circle-shaped loop, an ellipse-shaped loop, and the like), may be directed to enable the fastening of power source 118 on wearable electronic device strap 104 of wearable electronic device 100 (FIGS. 2B-2D).

Power source 118, which may be any type of power source known in the art, may be directed to electrically interact with the rechargeable battery within the cavity 106 of wearable electronic device case 102 (either in a wired or wireless manner), without interfering with the operation of one or more power-consuming component (e.g., sensors, screens, and the like), located on the wearable electronic device case 102.

In cases where the interaction between the power source 118 and the rechargeable battery is of the wired type, wearable electronic device charging unit 116 may further include a protrusion, e.g., protrusion 122, extending from one of its surfaces. Protrusion 122 enables connecting power source 118 to an electrical wire, for example, electrical wire 124, which is connected on its distal end to the rechargeable battery housed within wearable electronic device case 102, so as to transfer an electrical current from wearable electronic device charging unit 116 to the rechargeable battery. The electrical wire 124, which may be, for example, of a flexible material, a semi-flexible, and/or coated with isolated material, may further include a designated plug 126 (illustrated, for example, in FIGS. 2C and 3) situated at its distal end configured to enable the interaction of electrical wire 124 with the at least one electrical connector 108 and allow transfer of electrical current from wearable electronic device charging unit 116 to the rechargeable battery within cavity 106 of wearable electronic device case 102.

Figure 4:
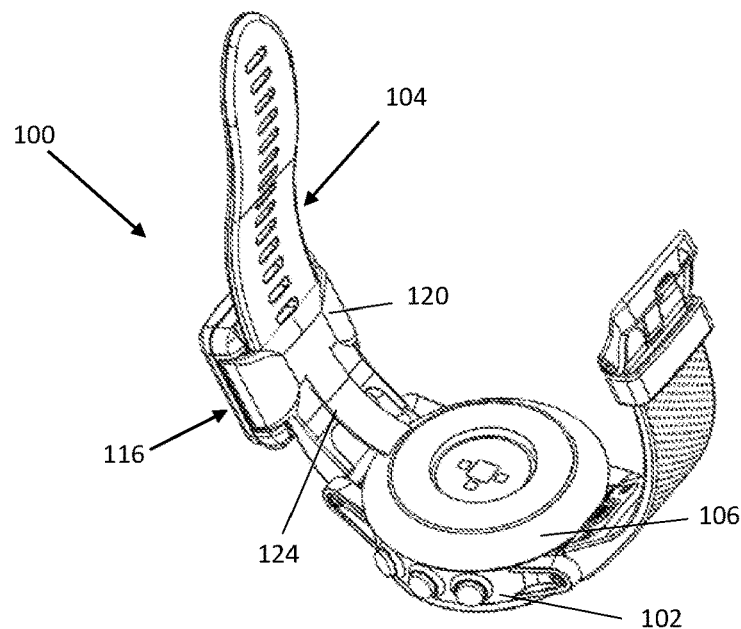

In some cases, as illustrated in FIG. 4, the electrical wire 124 may extend from wearable electronic device charging unit 116 to the rechargeable battery within cavity 106 of wearable electronic device case 102 in a concealed manner, without needing protrusion 122. In such cases, the electrical wire 124 extends between wearable electronic device charging unit 116 and the rechargeable battery within cavity 106 of wearable electronic device case 102 along the bottom surface of wearable electronic device strap 104 (including passage through securing element 120), without being visible.

Figure 5A:
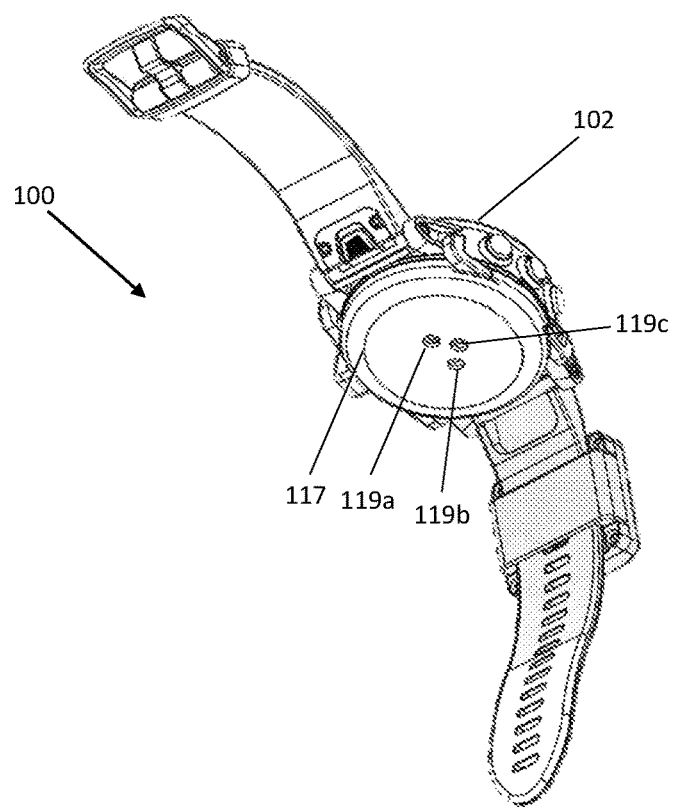
FIGS. 5A-5B are schematic illustrations of a wireless charger adapter positioned at the bottom surface of a wearable electronic device case, in accordance with the presently disclosed subject matter.
Figure 5B:
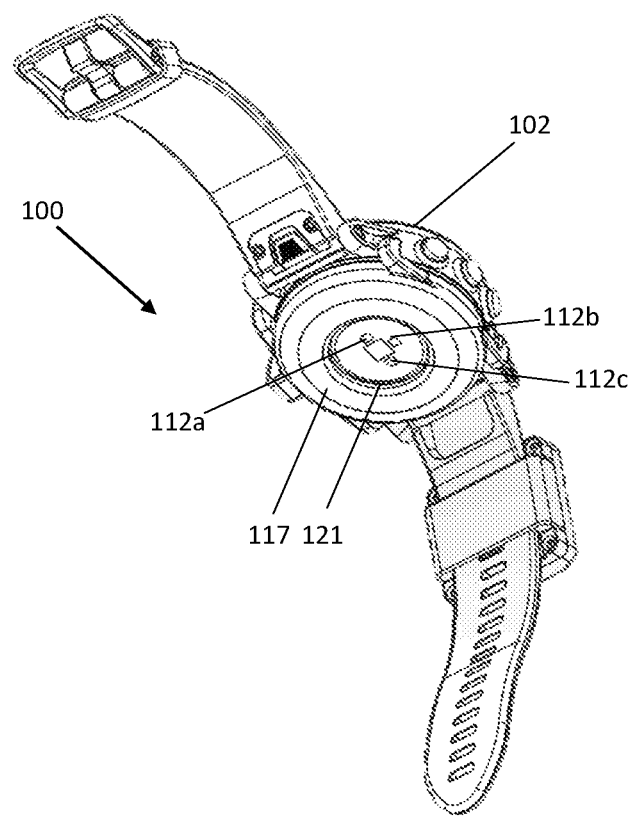

In cases where the interaction between the power source 118 and the rechargeable battery is done wirelessly, via, for example, an electromagnetic induction, the wearable electronic device case 102 may be connected to a wireless charger adapter 117 (illustrated in FIGS. 5A and 5B). The wireless charger adapter 117, which may be fitted on different surfaces of the wearable electronic device case 102 (e.g., bottom surface 110) using any fitting means known in the art (for example, mechanical fitting, magnets, fasteners, snaps, reusable adhesives, vacuum suction means, etc.), may include (i) an antenna, (ii) a number of passive conductive components, and (iii) an inductive coil (all not shown), which may be utilized to form an electrical induction through which power source 118 charges the rechargeable battery within wearable electronic device case 102.

The wireless charger adapter 117 can be in an electrical interaction with the power source 118 via, for example, one or more conductors (not shown), connected at one end to the power source 118 and at the other end to the inductive coil of the wireless charger adapter 117. For example, as an electrical current runs from power source 118, through the one or more conductors, to the inductive coil of the wireless charger adapter 117, a magnetic field is created at the proximity of the inductive coil. The created magnetic field causes voltage induction in the inductive coil, which inductively transfers power from the wireless charger adapter 117 to the rechargeable battery within wearable electronic device case 102.

In some cases, the one or more conductors involve two or more conductors directed to create a closed electrical circuit between the power source 118 and the rechargeable battery within cavity 106 of the wearable electronic device case 102. By not using a single conductor to create the aforementioned closed electrical circuit, the volume and thickness of each of the two or more conductors can be much thinner (enabling a more comfortable wearing of the wearable electronic device 100).

In some cases, the wireless charger adapter 117 may include a thermocouple placed close to the inductive coil of the wireless charger adapter 117. The thermocouple is directed to provide real-time temperature measurements of the wireless charger adapter's 117 surface and serve as a precaution against overheating damages that may occur in cases where the inductive coil of the wireless charger adapter 117 overheats during its operation.

In some cases, as illustrated in FIG. 5A, the wireless charger adapter 117 can include one or more apertures, for example, apertures 119a-119c, positioned correspondingly to the location of sensors 112a-112c, directed to enable sensors 112a-112c to operate without interference during charging. In other cases, as illustrated in FIG. 5B, the wireless charger adapter 117 may include a transparent region 121 corresponding to the location of sensors 112a-112c, such that sensors 112a-112c are not blocked by the wireless charger adapter 117 and can operate regularly during charging. It is to be noted that the relatively low number of components of wireless charger adapter 117 is intended to allow minimal volume and thickness of the wireless charger adapter 117, enabling comfortable wearing and a more natural look to the watch.

It is to be noted that the different fitting means allow the wireless charger adapter 117 to be fitted on any wearable electronic device known in the art.

In some cases, the inductive coil of the wireless charger adapter 117 may be attached to the bottom surface of the wearable electronic device case 102 using a fastening element, e.g., a magnet, or a designated mechanical fitting (made of plastic or other isolating material), which wraps the bottom surface of the wearable electronic device case 102 (e.g., by being snapped to the bottom surface of the wearable electronic device case 102), holding the inductive coil therebetween the surface of wearable electronic device case 102 and the designated mechanical fitting. In this manner we form a more reliable and mechanically safe connection. It is to be noted that in cases involve the use of the designated mechanical fitting, a multi-layered configuration composed of a first layer—the bottom surface of the wearable electronic device case 102, a second layer—the inductive coil, and a third layer—the fastening element, is formed. It should also be noted that the inductive coil can be wrapped with an additional fretic layer designed to direct the magnetic field generated in a specific direction.

In some cases, power source 118 may include an indicator indicative of the state (e.g., the remaining power) of the power source 118 or the rechargeable battery (once power source 118 is in electrical interaction with the rechargeable battery). The indicator may include at least one light source, for example, a light-emitting diode (LED), providing a visual display of the power state of the power source 118 or the rechargeable battery.

In some cases, power source 118 is situated within a designated housing made of, for example, rigid or semi-rigid material, directed to protect power source 118 from external hazards, such as weather conditions, water damages, and the like.

In some cases, referring to both types of electrical interaction between the power source 118 and the rechargeable battery within cavity 106 of wearable electronic device case 102 described therebefore, the electrical interaction is controlled by a designated button placed, for example, on either power source 118 or wearable electronic device case 102. The designated button may enable the user of the wearable electronic device 100 to initiate the charging operation of the rechargeable battery upon demand.

Attention is now drawn to the components of electronic device charging unit 116.

FIG. 6 is a block diagram schematically illustrating one example of the wearable electronic device charging unit 116, in accordance with the presently disclosed subject matter.

In accordance with the presently disclosed subject matter, wearable electronic device charging unit 116 can comprise a network interface 206. The network interface 206 (e.g., a network card, a Wi-Fi client, a Li-Fi client, 3G/4G client, or any other component), enables wearable electronic device charging unit 116 to communicate over a network with external systems and handles inbound and outbound communications from such systems. For example, wearable electronic device charging unit 116 can receive, through network interface 206, information regarding the current power level of the rechargeable battery within wearable electronic device case 102.

Wearable electronic device charging unit 116 can further comprise or be otherwise associated with a data repository 204 (e.g., a database, a storage system, a memory including Read Only Memory—ROM, Random Access Memory—RAM, or any other type of memory, etc.) configured to store data, optionally including, charging patterns, charging frequency, charging durations, prescheduled charging periods, etc. Data repository 204 can be further configured to enable retrieval and/or update and/or deletion of the stored data.

It is to be noted that in some cases, data repository 204 can be distributed, while the wearable electronic device charging unit 116 has access to the information stored thereon, e.g., via a wired or wireless network to which wearable electronic device charging unit 116 is able to connect (utilizing its network interface 206).

Wearable electronic device charging unit 116 further comprises processing circuitry 202. Processing circuitry 202 can be one or more processing units (e.g., central processing units), microprocessors, microcontrollers (e.g., microcontroller units (MCUs)) or any other computing devices or modules, including multiple and/or parallel and/or distributed processing units, which are adapted to independently or cooperatively process data for controlling relevant wearable electronic device charging unit 116 resources and for enabling operations related to wearable electronic device charging unit's 116 resources.

The processing circuitry 202 comprises a charging module 208, configured to perform a charging process, as further detailed herein, inter alia with reference to FIG. 7.

Turning to FIG. 7, there is shown a flowchart illustrating one example of a sequence of operations carried out for wearable electronic device charging, in accordance with the presently disclosed subject matter.

Accordingly, the wearable electronic device charging unit 116 can be configured to perform a charging process 300, e.g., using charging module 208.

For this purpose, during an electrical interaction between wearable electronic device charging unit 116 and the rechargeable battery of wearable electronic device case 102, wearable electronic device charging unit 116 obtains information from the rechargeable battery regarding its power level (block 302).

As the information regarding the rechargeable battery's power level reaches wearable electronic device charging unit 116, wearable electronic device charging unit 116, through its charging module 208, compares the information to a predefined threshold or a threshold range (block 304). In cases where the rechargeable battery's power level is below the predefined threshold or the threshold range, wearable electronic device charging unit 116 initiates an electrical current transfer from wearable electronic device charging unit 116 to the rechargeable battery of wearable electronic device 100 (block 306).

Once the power level of the rechargeable battery reaches, for example, a maximum value or a predefined value, wearable electronic device charging unit 116 terminates the electrical current transferring.

By way of example, in accordance with the example described therebefore, during the electrical interaction between the wearable electronic device charging unit 116 and the rechargeable battery of smartwatch 100, the wearable electronic device charging unit 116 obtains information from the rechargeable battery indicating that the rechargeable battery's power level is at 50%.

The wearable electronic device charging unit 116, through its charging module 208, compares the rechargeable battery's power level (50%) to a predefined threshold (75%). Since the rechargeable battery's power level is below the predefined threshold (50% vs. 75%), the wearable electronic device charging unit 116 initiates an electrical current transfer from it to the rechargeable battery.

Once the rechargeable battery's power level reaches the rechargeable battery's maximum value of 100%, the electrical current transfer is terminated.

In another embodiment, the rechargeable battery of wearable electronic device 100 may be connected to an inner charging circuit located within the wearable electronic device 100, such that once an electrical interaction between wearable electronic device charging unit 116 and the rechargeable battery is assembled, the inner charging circuit controls the rechargeable battery's charging by regulating the electric flow transferred from the wearable electronic device charging unit 116 to the rechargeable battery (i.e., opening or closing the electrical flow by switching from a closed electrical circuit to an open electrical circuit).

It is to be noted, with reference to FIG. 7, that some of the blocks can be integrated into a consolidated block or can be broken down to a few blocks and/or other blocks may be added. It is to be further noted that some of the blocks are optional. It should be also noted that whilst the flow diagram is described also with reference to the system elements that realizes them, this is by no means binding, and the blocks can be performed by elements other than those described herein.

It is to be understood that the presently disclosed subject matter is not limited in its application to the details set forth in the description contained herein or illustrated in the drawings. The presently disclosed subject matter is capable of other embodiments and of being practiced and carried out in various ways. Hence, it is to be understood that the phraseology and terminology employed herein are for the purpose of description and should not be regarded as limiting. As such, those skilled in the art will appreciate that the conception upon which this disclosure is based may readily be utilized as a basis for designing other structures, methods, and systems for carrying out the several purposes of the present presently disclosed subject matter.

It will also be understood that the system according to the presently disclosed subject matter can be implemented, at least partly, as a suitably programmed computer. Likewise, the presently disclosed subject matter contemplates a computer program being readable by a computer for executing the disclosed method. The presently disclosed subject matter further contemplates a machine-readable memory tangibly embodying a program of instructions executable by the machine for executing the disclosed method.

The invention claimed is:

1. A wearable electronic device charging unit configured to be fastened onto a wearable electronic device strap, attached to a wearable electronic device case, the wearable electronic device charging unit comprising:
   a power source; and,
   at least one securing element coupled to said power source configured to attach said power source onto said wearable electronic device strap, without being physically coupled to said wearable electronic device case via same strap medium;
   wherein said power source is configured to be in an electrical communication with a rechargeable battery located within said wearable electronic device case so as to recharge said rechargeable battery, as said wearable electronic device is wrapped around a user's wrist, without interfering with the operation of one or more power-consuming components located on said wearable electronic device case.

2. The wearable electronic device charging unit of claim 1, wherein said electrical communication is achieved through an electrical wire being in communication with said power source, configured to connect said power source to the rechargeable battery.

3. The wearable electronic device charging unit of claim 2, wherein said connection of said power source to said rechargeable battery is formed at the bottom or side surfaces of said wearable electronic device case.

4. The wearable electronic device charging unit of claim 2, wherein said wearable electronic device case includes at least one electrical connector at its bottom or side surfaces configured to enable said electrical wire to interact with said rechargeable battery located within said wearable electronic device case.

5. The wearable electronic device charging unit of claim 2, wherein said electrical wire extends between said wearable electronic device charging unit and said rechargeable battery of said wearable electronic device case along the bottom surface of said wearable electronic device strap, without being visible, as said wearable electronic device is wrapped around a user's wrist.

6. The wearable electronic device charging unit of claim 1, wherein said charge involves wireless charging.

7. The wearable electronic device charging unit of claim 6, wherein said wireless charging is achieved using a wireless charger adapter containing an inductive coil directed to form an electrical induction through which the power source charges the rechargeable battery within the wearable electronic device case.

8. The wearable electronic device charging unit of claim 7, wherein said wireless charger adapter includes one or more apertures positioned correspondingly to the location of said one or more power-consuming components.

9. The wearable electronic device charging unit of claim 7, wherein the inductive coil is attached to the bottom surface of the wearable electronic device case element using a designated mechanical fitting which wraps the bottom surface of the wearable electronic device case, holding the inductive coil therebetween the surface of wearable electronic device case and the designated mechanical fitting.

10. A wearable electronic device charging unit configured to be fastened onto a wearable electronic device strap attached to a wearable electronic device case, without being physically coupled to said wearable electronic device case via same strap medium, the wearable electronic device charging unit comprising:
    a power source configured to be in an electrical communication with a rechargeable battery located within said wearable electronic device case so as to recharge said rechargeable battery, as said wearable electronic device is wrapped around a user's wrist without interfering with the operation of one or more sensors located on said wearable electronic device case;
    at least one securing element coupled to said power source configured to attach said power source onto said wearable electronic device strap; and, a processing circuitry configured to:
        obtain information from said rechargeable battery located within said wearable electronic device case regarding its power level;
        compare said information to a threshold; and,
        based on the result of the comparison, initiate an electrical current transferring from said wearable electronic device charging unit to said rechargeable battery.

11. The wearable electronic device charging unit of claim 10, wherein said electrical communication is achieved through an electrical wire being in communication with said power source configured to connect said power source to the rechargeable battery.

12. The wearable electronic device charging unit of claim 11, wherein said connection of said power source to said rechargeable battery is formed at the bottom or side surfaces of said wearable electronic device case.

13. The wearable electronic device charging unit of claim 11, wherein said wearable electronic device case includes at least one electrical connector at its bottom or side surfaces configured to enable said electrical wire to interact with said rechargeable battery located within said wearable electronic device case.

14. The wearable electronic device charging unit of claim 11, wherein said electrical wire includes a designated plug at its distal end configured to interact with said at least one electrical connector.

15. The wearable electronic device charging unit of claim 11, wherein said electrical wire extends between said wearable electronic device charging unit and said rechargeable battery of said wearable electronic device case along the bottom surface of said wearable electronic device strap, without being visible, as said wearable electronic device is wrapped around a user's wrist.

16. The wearable electronic device charging unit of claim 10, wherein said power source further includes an indicator indicative of the state of said rechargeable battery.

17. The wearable electronic device charging unit of claim 10, wherein said charge involves wireless charging.

18. The wearable electronic device charging unit of claim 17, wherein said wireless charging is achieved using a wireless charger adapter containing an inductive coil directed to form an electrical induction through which the power source charges the rechargeable battery within the wearable electronic device case.

19. The wearable electronic device charging unit of claim 18, wherein the inductive coil is attached to the bottom surface of the wearable electronic device case element using a designated mechanical fitting which wraps the bottom surface of the wearable electronic device case, holding the inductive coil therebetween the surface of wearable electronic device case and the designated mechanical fitting.

20. The wearable electronic device charging unit of claim 18, wherein said wireless charger adapter includes one or more apertures positioned correspondingly to the location of said one or more power-consuming components.

* * * * *